United States Patent [19]

Noiles

[11] Patent Number: 4,790,852
[45] Date of Patent: Dec. 13, 1988

[54] SLEEVES FOR AFFIXING ARTIFICIAL JOINTS TO BONE

[75] Inventor: Douglas G. Noiles, New Canaan, Conn.

[73] Assignee: Joint Medical Products Corporation, Stamford, Conn.

[21] Appl. No.: 907,746

[22] Filed: Sep. 15, 1986

[51] Int. Cl.$^4$ .......................... A61F 2/30; A61F 2/32
[52] U.S. Cl. ........................................ 623/18; 623/16; 623/23
[58] Field of Search .................................... 623/16–23

[56] References Cited

U.S. PATENT DOCUMENTS 3,894,297  7/1975  Miltelmeier et al. ................. 623/23
4,670,015  6/1987  Freeman ............................... 623/23

FOREIGN PATENT DOCUMENTS

WO85/03426  8/1985  PCT Int'l Appl. .

OTHER PUBLICATIONS

"The Freeman Total Hip System," Corin Medical Limited, Gloucestershire, England, 1985.
Freeman, M. A. R., "Why Resect the Neck?", *The Journal of Bone and Joint Surgery*, vol. 68–B, No. 3, May 1986, pp. 346–349.
Freeman et al., in *The Young Patient with Degenerative Hip Disease*, Sevastik J. Goldie I (ed.), Stockholm, Sweden, 1986, pp. 281–292.

*Primary Examiner*—Richard J. Apley
*Assistant Examiner*—David J. Isabella
*Attorney, Agent, or Firm*—Maurice M. Klee

[57] ABSTRACT

Sleeve for affixing artificial joints to bone are provided which include a cone-shaped portion centered on the sleeve's longitudinal axis and a protruding portion offset from the longitudinal axis having an elliptically-shaped leading edge. Cavities which are essentially a perfect match to the shape of the sleeve can be readily formed in the patient's bone. The shape of the cavities generally correspond to the inside shape of the patient's hard bone. Accordingly, when implanted, the sleeves transfer stresses from the prosthesis to hard bone as is desired.

14 Claims, 4 Drawing Sheets

SLEEVES FOR AFFIXING ARTIFICIAL JOINTS TO BONE

BACKGROUND OF THE INVENTION

1. Field of the Invention

This invention relates to the field of artificial joints and, in particular, to apparatus for affixing such joints to bone.

2. Description of the Prior Art

In PCT publication number WO 85/03426 entitled "Apparatus for Affixing a Prosthesis to Bone," various sleeves for affixing artificial joints to bone are described having the following characteristics: (1) the outer surface of the sleeve is contoured so as to mate with the inner surface of the patient's hard bone; and (2) the outer surface of the sleeve comprises a plurality of spaced, outwardly extending shoulders, the purpose of which is to transfer stresses from the prosthesis to the hard bone in a manner similar to that in which stresses are transferred from soft bone to hard bone.

The present invention is directed to improving the utility of the sleeves disclosed in the foregoing PCT publication. While it is possible to provide sleeves of the type disclosed in the PCT publication which approximate the hard bone contours of individual patients, sleeves of this type do not have a regular geometric shape, and therefore surgeons have found it difficult to prepare patient's bones for receiving such sleeves using standard, or even special, surgical tools for cutting and reaming bone.

SUMMARY OF THE INVENTION

In view of the foregoing state of the art, it is an object of this invention to provide sleeves for affixing artificial joints to bone which have outer surfaces which (1) are contoured so that they generally correspond to the inner surfaces of the hard bones of a variety of patients, notwithstanding the anatomical variability from patient to patient, (2) are contoured so that the surgeon can readily and precisely prepare a cavity in the patient's bone for receiving the sleeve, and (3) include a plurality of spaced-apart, outwardly-extending terraces which can cut into the bone, and/or encourage bone ingrowth, and which transfer stresses to the patient's bone in a manner which generally corresponds to the manner in which stresses are transferred from soft bone to hard bone.

More generally, in contrast to the approach of the above-referenced PCT publication, wherein the shape of the patient's hard bone defined the shape of the prosthesis as well as the shape of the cavity to be formed in the patient's bone, the approach of the present invention is to provide a prosthesis shape which can readily be accurately and reproducibly formed in the patient's bone and which in general approximates the shape of the hard bone, and then match the patient's bone to the prosthesis by forming a cavity in the bone which exactly matches the shape of the prosthesis.

To accomplish the foregoing, the invention provides sleeves for implantation in bone having terraced outer surfaces, the perimeters of the outer edges of the terraces having specified shapes so as to satisfy the twin goals of approximating hardbone contours and providing an overall shape for the prosthesis which can be readily cut in the patient's bone by the surgeon.

In particular, the terraces nearest to the motion surface of the joint have a first set of perimeters, while those away from the joint motion surface have a second set of perimeters. All of the perimeters lie in planes which are substantially perpendicular to the longitudinal axis of the sleeve.

The perimeters of the first set are composed of a portion of a circle and a portion of an ellipse. The circle portions are centered on the sleeve's longitudinal axis. The radii of the circles increase as one moves towards the joint motion surface so that the envelope of the circles is a cone. In practice, a total cone angle of, for example, 6° has been found suitable.

Ellipses having the same major and minor axes, i.e., the same shape, are used for each terrace, but the portion of the ellipse used increases from terrace to terrace as one moves towards the joint motion surface until half an ellipse has been used. Thereafter, half an ellipse is used for all terraces closer to the joint motion surface, the halves of ellipses being connected to the circle portions of the perimeters by two lines which are parallel to the ellipse's major axis and tangent to the ellipse at the ends of its minor axis. Optionally, to facilitate the manufacturing process, the junctions between the portion of the ellipse and the portion of the circle or between the two straight lines and the portion of the circle, as the case may be, may be rounded with a portion of a circle of a suitable radius to produce a smooth transition into the circle portion of the perimeter.

The major axes of all of the ellipses lie in a common plane, and all of the axes are orthogonal to the sleeve's longitudinal axis. The portion of the ellipse used for each terrace includes a vertex of the ellipse. The vertices for the different terraces lie along a line which intersects the sleeve's longitudinal axis at a predetermined angle determined by the tool used to ream the patient's bone (see discussion below).

The second set of perimeters are composed of circles centered on the sleeve's longitudinal axis. The radii of the circles increases as one moves towards the joint motion surface so that the circles of the second set of perimeters lie on the same cone as the circle portions of the first set of perimeters.

The transition from the first set of perimeters to the second set of perimeters occurs at the level where the line through the vertices of the ellipses first intersects the cone defined by the circular portions of the first set of perimeters. For some applications, a relatively short sleeve may be desirable, in which case only a first set of perimeters will be used and a transition from the first to the second set of perimeters will not occur.

As discussed below, by using perimeters of the foregoing shapes, the prosthesis can readily be given an overall shape which generally corresponds to the shapes of hard bones encountered in practice. This correspondence can be further improved by supplying the surgeon with families of sleeves (see discussion below).

Moreover, the surgeon can readily prepare the patient's bone for receiving the prosthesis. Specifically, a cavity for receiving the second set of perimeters and the circular portions of the first set of perimeters can be formed in the patient's bone using a conventional conical reamer, and a further cavity, connected to the conical cavity, for receiving the ellipse portions of the first set of perimeters, as well as the connection between those portions and the circular portions, can be formed using the tool shown in FIG. 6 (see discussion below). In general, both cavities are made somewhat smaller than the prosthesis so that the prosthesis fits tightly in the patient's bone when implanted.

The combination of the two cavities produces an overall cavity which in essence perfectly matches the outside shape of the sleeve. This perfect match, in turn, produces a strong, initial, mechanical fixation of the sleeve to the patient's bone and intimate contact between the sleeve and the bone so as to encourage bone ingrowth.

In connection with these latter aspects, in certain embodiments of the invention, the outside surface of the sleeve is undercut between terraces so as to accentuate the ability of the outer edges of the terraces to cut bone. Such cutting occurs as the sleeve is forced into the cavity formed in the patient's bone. The cutting results in the generation of bone chips in the regions between the terraces which further enhances bone ingrowth into these areas.

In connection with other embodiments of the invention, the outside surface of the prosthesis can be covered with a porous coating to further enhance bone ingrowth (see FIG. 2).

The accompanying drawings, which are incorporated in and constitute part of the specification, illustrate the preferred embodiments of the invention, and together with the description, serve to explain the principles of the invention.

DESCRIPTION OF THE PREFERRED EMBODIMENTS

Figure 1:
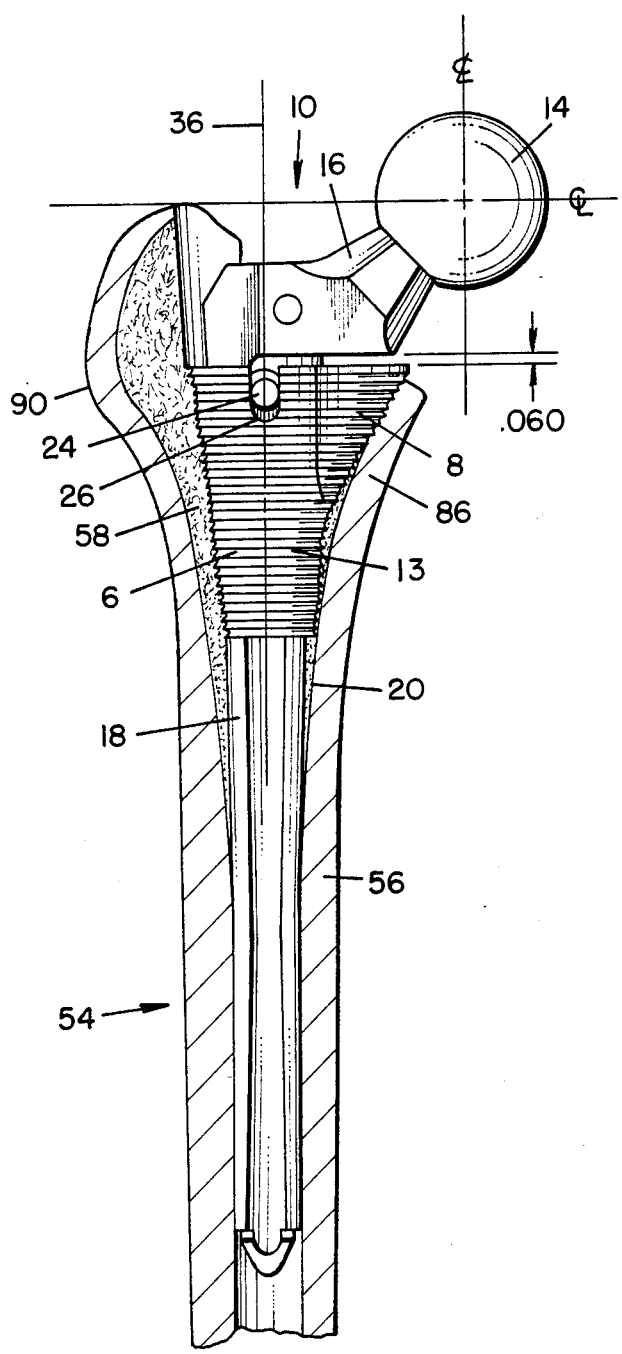
FIG. 1 is an anterior view showing a femoral prosthesis employing a sleeve constructed in accordance with the present invention which has been implanted in a patient's femur. The femur is shown in section to illustrate the relationship between the prosthesis and the soft and hard bone portions of the femur.

With reference now to the drawings, wherein like reference characters designate like or corresponding parts throughout the several views, there is shown in FIG. 1, a femoral component 10 of an artificial hip joint employing sleeve 13 constructed in accordance with the present invention. Sleeve 13 includes cone portion 6 centered on the sleeve's longitudinal axis 36 and protruding portion 8 which is offset from and extends away from the longitudinal axis.

Femoral component 10 is implanted in the patient's femur 54 which has an outer shell 56 of hard bone surrounding an inner core 58 of soft bone. Motion of the joint occurs about ball 14. The ball is connected to neck 16 which, in turn, is connected to stem 18.

Stem 18 and sleeve 13 mate by means of complementary locking tapers on outside surface 20 of the stem and inside surface 22 of the sleeve. In addition, the stem is provided with pins 24 which mate with slots 26 in the sleeve so as to prevent the stem from rotating within the sleeve prior to full locking engagement of the tapers. To insure full engagement of the locking tapers notwithstanding slight variations in the components as a result of the manufacturing process, the tapers on the sleeve and the stem are nominally sized to provide a gap of approximately 0.060 inches between the bottom of neck 16 and the top of the sleeve. Similarly, pin 24 is spaced a nominal 0.060 inches from the bottom of slot 26.

Figure 2:
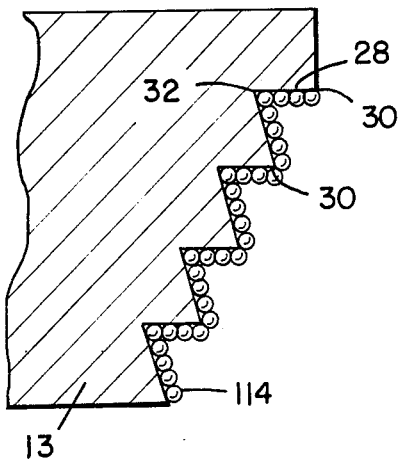
FIG. 2 is a magnified view of a section through the outside surface of the sleeve of the present invention.
Figure 3:
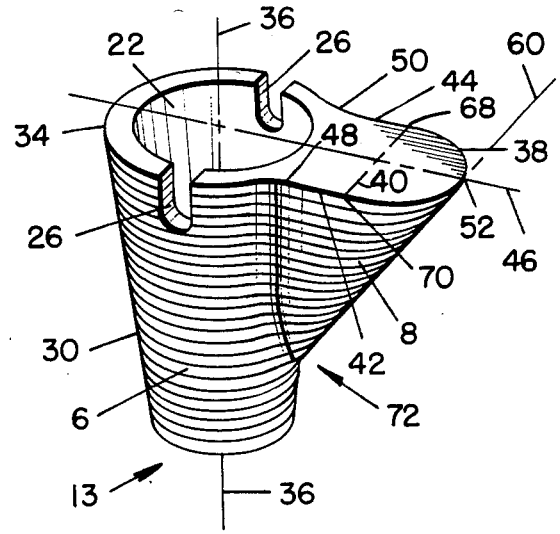
FIG. 3 is a perspective view of the sleeve of the present invention.

The outside surface of sleeve 13 includes a plurality of terraces 28 having outer and inner edges 30 and 32, respectively (see FIG. 2). The vertical spacing between terraces is preferably on the order of between approximately 0.5 mm and approximately 3.0 mm. The depth of the terraces is preferably on the order of between approximately 0.2 mm and approximately 1.5 mm. As shown in FIG. 3, the perimeters of outer edges 30 lie in planes which are substantially orthogonal to the longitudinal axis 36 of the sleeve.

At the upper portion of sleeve 13, the perimeters of outer edges 30 include circular portions 34 centered on longitudinal axis 36 and elliptical portions 38 which include vertices 52. The radii of circular portions 34 decrease as one moves away from the top of the sleeve, the cone angle of these portions, as discussed above, being approximately 6°. Similarly, the distances of vertices 52 from axis 36 decrease as one moves away from the top of the sleeve. Elliptical portions 38, however, all have the same shape in the sense that they are all portions of a common ellipse.

As shown in FIG. 3, vertices 52 lie on a common line 60 which intersects axis 36 at a predetermined angle. The angle is chosen so that the overall shape of the sleeve generally corresponds to the anatomical hard bone shapes encountered in practice. For example, for femoral prostheses, an angle of approximately 32° has been found suitable for achieving the desired matching. Other angles, of course, can be used. As discussed below, the angle between line 60 and axis 36 is also the angle between shaft 62 and cutter 64 of tool 66 (see FIG. 6).

As further shown in FIG. 3, the uppermost perimeter includes a full half of an ellipse extending between ends 68 and 70 of the ellipse's minor axis 40. The half ellipse is connected to the circular portion 34 of the perimeter by line segments 42 and 44. These line segments are tangent to the ellipse at points 68 and 70, and thus are parallel to the major axis of the ellipse. The major axis lies on line 46 which is orthogonal to axis 36. As discussed above, the junction between line segments 42 and 44 and circular portion 34 are rounded as shown at 48 and 50 to facilitate manufacture.

To maintain vertices 52 on line 60 for perimeters below the uppermost perimeter, shorter line segments 42 and 44 are first used and then less than a full half of an ellipse. Rounded junctions 48 and 50 can also be used with these smaller perimeters.

At the lower portion of sleeve 13, the perimeters of outer edges 30 are circles with the radii of the circles decreasing as one moves towards the bottom of the sleeve so that outer edges of these perimeters lie on the same cone as portions 34 of the upper perimeters. The transition between the upper perimeters and the lower perimeters occurs at the intersection of line 60 with the cone defined by portions 34 of the upper perimeters. This intersection is shown at 72 in FIG. 3.

Figure 5:
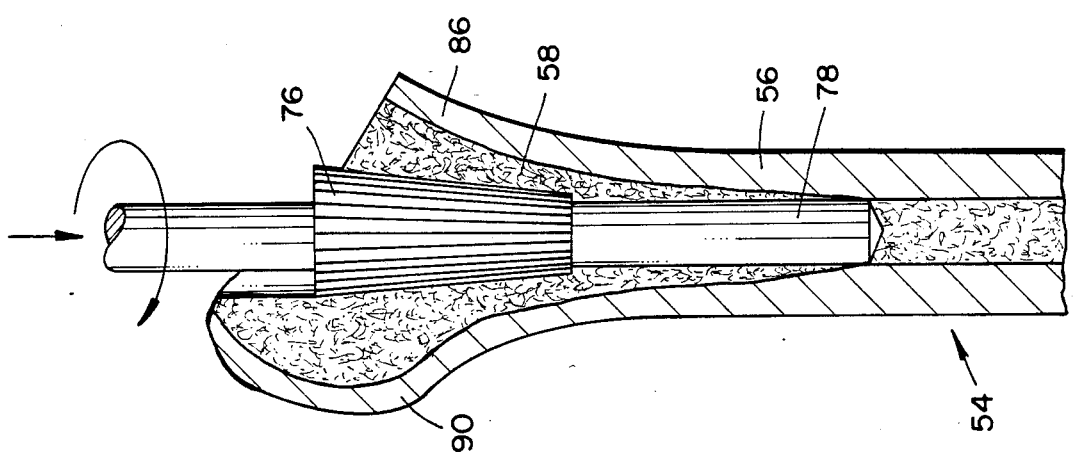
FIG. 5 is an anterior view, partially in section, illustrating the reaming of the patient's femur with a conical reamer.
Figure 4:
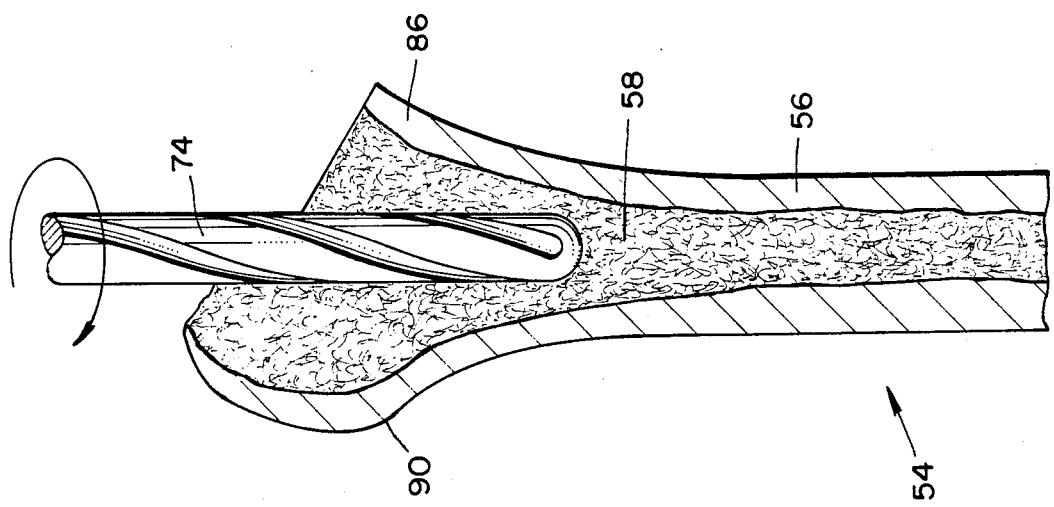
FIG. 4 is an anterior view, partially in section, illustrating the reaming of the patient's femur with a straight reamer.

Turning now to the process for implanting sleeve 13, as shown in FIG. 4, a straight hole for receiving stem 18 is formed in the patient's femur 54 using straight reamer 74. Next, as shown in FIG. 5, a conical cavity for receiving cone portion 6 of sleeve 13 is formed using conical reamer 76. This reamer includes a pilot shaft 78 for aligning the conical cavity with the straight hole formed by straight reamer 74. The conical cavity has the same cone angle as the circular portions of sleeve 13, e.g., 6°. It is made smaller than the sleeve, e.g., by approximately 0.5 mm, so that the sleeve will fit tightly in the cavity when implanted.

Figure 7:
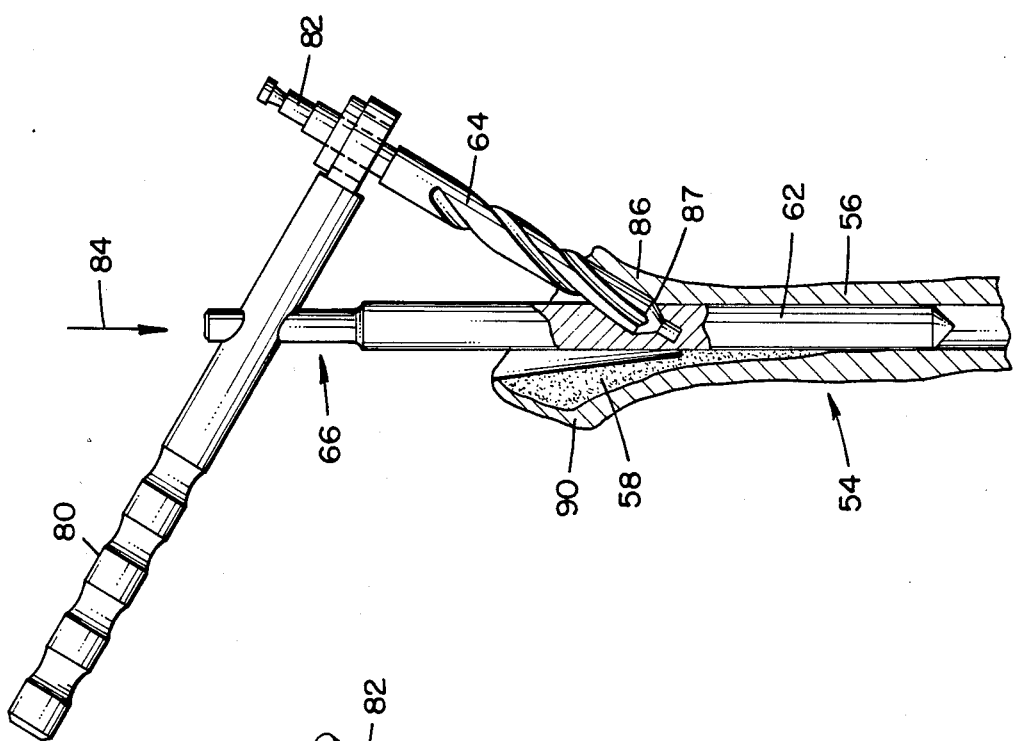
FIG. 7 is an anterior view, partially in section, illustrating the cutting of the patient's femur with the tool of FIG. 6.
Figure 6:
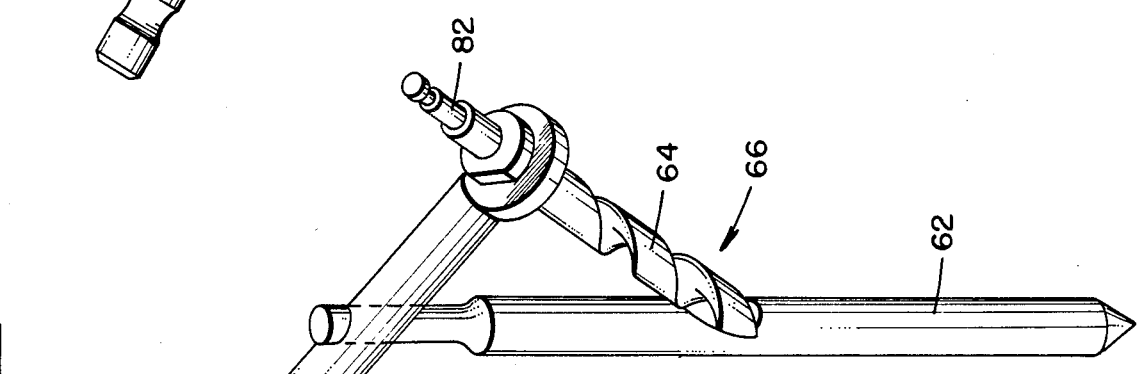
FIG. 6 is a perspective view of a suitable tool for cutting a cavity in the patient's femur for the protruding portion of the sleeve of the present invention.
Figure 10:
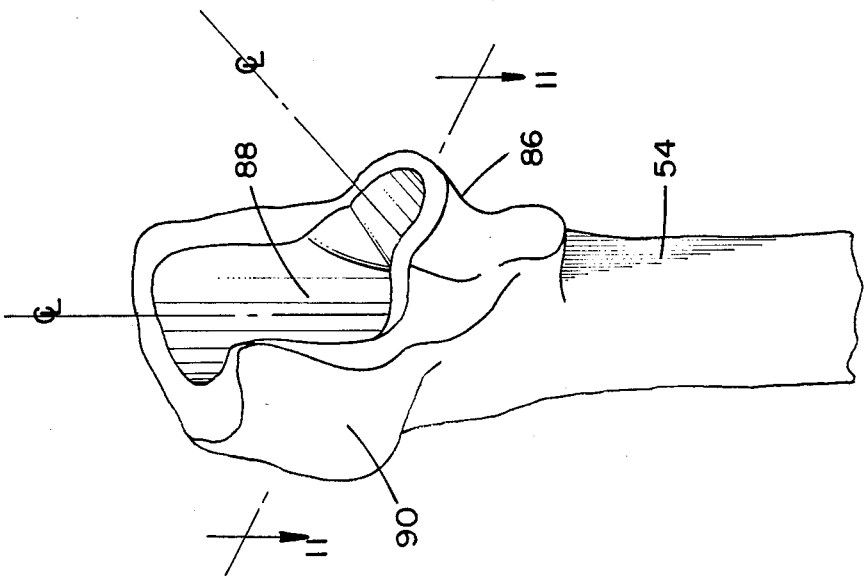
FIG. 10 is a perspective view of a cavity in a patient's femur which has been reamed to receive a sleeve constructed in accordance with the present invention. The two center lines shown in this figure correspond to the center lines of the conical reamer and cutter shown in FIGS. 5 and 7.

Next, a cavity for receiving protruding portion 8 of sleeve 13 is formed using tool 66 shown in FIG. 6. Tool 66 includes pilot shaft 62 for aligning the tool with the straight hole formed by straight reamer 74. It also includes cutter 64 for cutting the cavity and handle 80 for manipulating and stabilizing the tool as the reaming is performed. Cutter 64 includes fitting 82 for connection to a suitable power source for rotating the bit, e.g., a pneumatic power source. As shown in FIG. 7, tool 66 is moved downward (see arrow 84) until the surgeon is satisfied that cutter 64 has reached and prepared a suitable bed or seat for portion 8 of sleeve 13 in the hard bone in the region known as the calcar 86.

Figure 11:
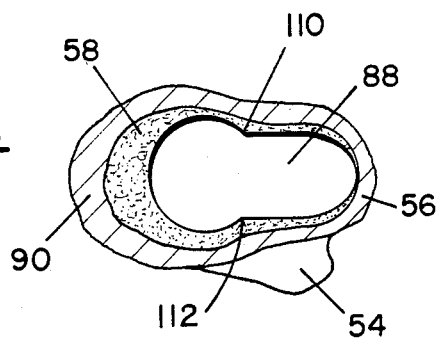
FIG. 11 is a cross-sectional view along lines 11—11 in FIG. 10.

Conical reamer 76 and cutter 64 are sized so that the finished cavity formed in the femur generally corresponds to the inner surface of the femur's hard bone. This correspondence can best be seen in FIG. 11. As shown therein, cavity 88 approximates the inner contours of hard bone 56, the maximum separation between the cavity and the hard bone occurring in the region of the femur's greater trochanter 90. Significantly, for physiological and anatomical reasons, it is preferred that the major stress transfers from the sleeve to the femur be in the region of the calcar 86, not the greater trochanter 90, and thus the somewhat greater separation of the cavity, and thus the sleeve, from the patient's hard bone in the region of the greater trochanter is acceptable.

In practice, sets of conical reamers 76 and cutting tools 66 are supplied to the surgeon so that femurs of various sizes can be prepared to receive sleeve 13. Sets of sleeves of different sizes to match the tools 66 are also provided.

For example, a set of conical reamers having maximum diameters of approximately from 17 mm to 25 mm in 2 mm increments in combination with a corresponding set of cutting tools having cutting diameters of approximately from 8 mm to 18 mm in 2 mm increments are suitable for preparing the great majority of femurs encountered in practice. A suitable set of sleeves corresponding to these tools can have maximum diameters of circle portions 34 ranging approximately from 17 mm to 25 mm in 2 mm increments, major axes for elliptical portions 38 approximately from 9 mm to 21 mm in approximately 2.3 mm increments for a 32° angle between line 60 and longitudinal axis 36, minor axes 40 approximately from 8 mm to 18 mm in 2 mm increments, and sleeve heights ranging approximately from 20 mm to 50 mm. Other sets of reamers, tools and sleeves, of course, can be used and will be readily apparent to persons skilled in the art in view of the present disclosure.

The diameter of cutter 64 and the angle between cutter 64 and shaft 62 determine the major and minor axes of elliptical portions 38 of the perimeters of the outer edges 30 of terraces 28 of sleeve 13. Specifically, for an exact fit of the protruding portion of the sleeve in the cavity formed by cutter 64, the minor axis equals the cutter diameter, while the major axis equals the cutter diameter divided by the cosine of the angle between cutter 64 and shaft 62. In practice, the major and minor axes of elliptical portion 38 are made slightly larger e.g., on the order of 0.5 mm, to ensure a tight fit.

Figure 12:
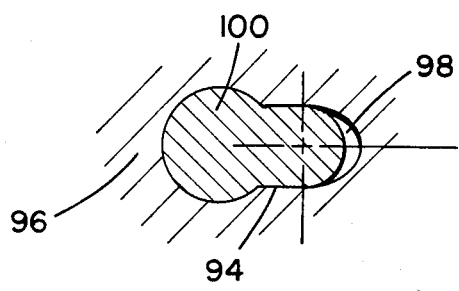
FIGS. 12 and 13 schematically illustrate the criticality of using an elliptical contour in constructing the protruding portion of the sleeve.
Figure 13:
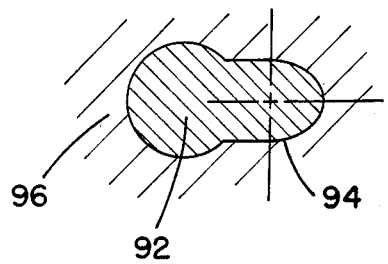

The calcar in an intact natural bone is highly stressed. Because bone maintains vitality where it is loaded, and atrophies where it is not loaded, it is important to transfer load from sleeve 13 to calcar 86. It is thus critical to use an ellipse for portions 38 of the outer perimeters of terraces 28 in order to achieve a geometric match between the shape of the sleeve and the shape of the cavity formed by tool 66. Specifically, the obvious choice for this contour—a circle—results in a significant mismatch between the prosthesis and the cavity. This criticality is illustrated in FIGS. 12 and 13. As shown therein, prosthesis 92, which employs an elliptical contour, fills cavity 94 in bone 96, while prosthesis 100, which employs a circular contour, leaves a substantial gap 98 between its outer edge and the inside surface of the cavity.

Returning to the implantation process, once the patient's bone has been reamed with conical reamer 76 and cut with tool 66, the surgeon is ready to implant sleeve 13. In order to further improve the match between the prosthetic sleeve and the cavity in an individual femur, it is preferred to provide the surgeon with a family of sleeves, e.g., five sleeves, which differ from one another with regard to the extent to which protruding portion 8 extends away from longitudinal axis 36. (Note that all of the members of the family have the same basic dimensions corresponding to the size of the conical reamer 76 and cutter 64 used to prepare the cavity, i.e., the same cone angle, the same major and minor axes for elliptical portions 38, the same maximum size for circular portion 34, and the same overall sleeve height.)

Figure 8:
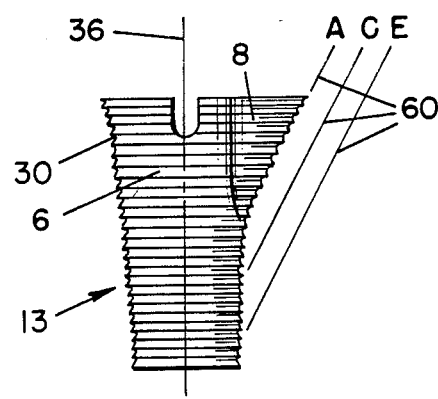
FIG. 8 is an anterior view schematically illustrating a family of sleeves having differing protruding portions.

Such a family is schematically illustrated in FIG. 8, where the letters A, C and E designate three sleeves having lines 60 progressively further from the sleeve's longitudinal axis. The differences between the sleeves is achieved by using longer line segments 42 and 44 for the sleeves having line 60 further from longitudinal axis 36. By selecting among the members of the family, the surgeon is able to compensate for differences in the amount of downward movement of tool 66 needed to reach a sufficient amount of hard bone in the region of calcar 86.

Figure 9:
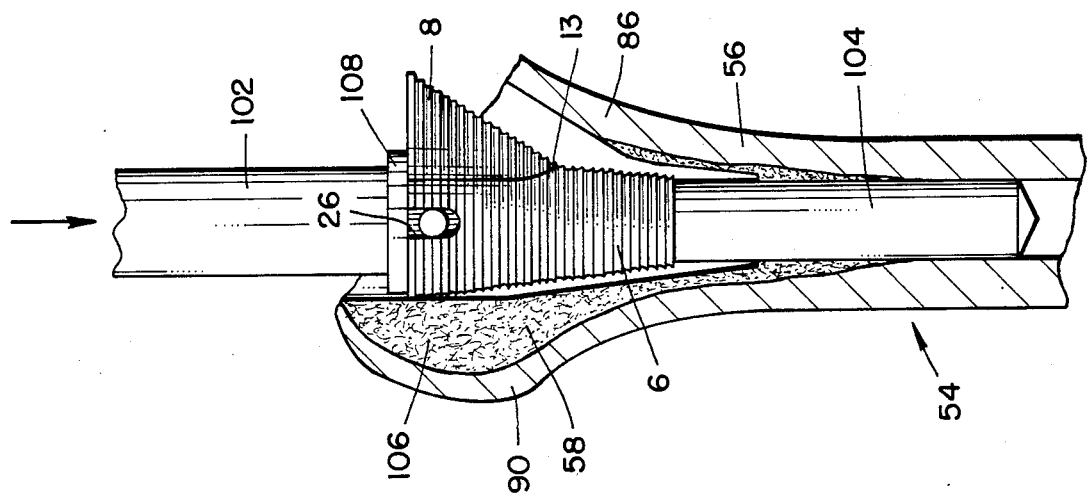
FIG. 9 is an anterior view, partially in section, illustrating the implantation of a sleeve in a patient's femur.

Once the proper sleeve for the patient has been chosen, implantation is performed using tool 102 (see FIG. 9). This tool includes pilot shaft 104, which is received in the straight hole formed by straight reamer 74, pins 106, which are received in slots 26 in sleeve 13, and flange 108 which contacts the top of the sleeve. Using this tool, sleeve 13 is driven into the prepared cavity.

As it moves into place, the sleeve, being slightly bigger than the cavity, cuts into the cavity thus generating crushed bone and bone chips at the prosthesis-bone interface. Cutting and crushing also occurs at corners 110 and 112 (see FIG. 11), where rounded corners 48 and 50 of sleeve 13 do not precisely match the prepared cavity. There may also be a small amount of bone projecting into the cavity in the region identified by the number 87 in FIG. 7 as a result of the construction of tool 66. This amount of bone is easily crushed as sleeve 13 is completed seated in the cavity. The generation of bone residue by the cutting and crushing at the foregoing locations is of value since it promotes the bone ingrowth process at the prosthesis-bone interface.

To enhance the ability of the sleeve to cut bone, it is preferred to undercut the outer surface of sleeve 13 between terraces 28. Specifically, as shown in FIG. 2, the outer surface is formed with inner edge 32 of each terrace 28 located closer to the sleeve's longitudinal axis than outer edge 30 of the next lower terrace.

As also shown in FIG. 2, to further enhance bone ingrowth, the outer surface of the sleeve can be porous coated using small balls 114 composed of the same metal as that used to form sleeve 13, e.g., a surgically implantable alloy such as a titanium alloy containing 6% aluminum and 4% vanadium or chemically pure titanium (see ASTM Spec. Nos. F136-79 and F67-83). By using a single layer of balls (see FIG. 2), the benefits of bone ingrowth can be achieved without sacrificing the benefits resulting from terracing and undercutting the outer surface of the sleeve.

The sleeves of the present invention can be formed using computer controlled machine tools. Alternatively, a master can be prepared using such tools, molds can be prepared from the master, and the finished parts can be cast using the molds. Porous coating of the sleeves can be performed using standard techniques such as by heating the coated sleeve to fuse the balls and the sleeve together.

Figure 14:
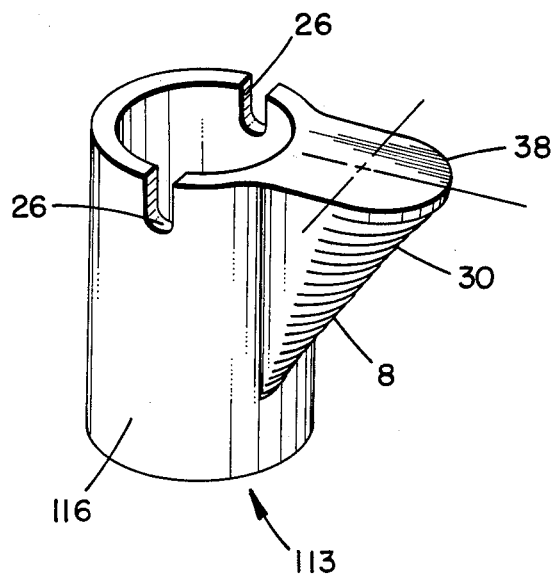
FIG. 14 illustrates an alternate embodiment of the invention employing a protruding portion in combination with a straight cylinder.

Although specific embodiments of the invention have been described and illustrated, it is to be understood that modifications can be made without departing from the invention's spirit and scope. For example, FIG. 14 shows modified sleeve 113 wherein a straight cylinder 116 has been substituted for cone portion 6 of sleeve 13. For this sleeve, only elliptical portion 38 of protruding portion 8 is terraced, although the remainder of the sleeve could be terraced, if desired, by means of undercutting.

Along these same lines, although the invention has been illustrated in the context of a femoral prosthesis, it is also applicable to other artificial joints, such as, shoulder and knee joints. In the latter case and for an implantation in the patient's tibia, the sleeve can be formed with two protruding portions extending from opposite sides of the sleeve. Other modifications and applications will be recognized by persons skilled in the art in view of the present disclosure.

What is claimed is:

1. A sleeve for affixing a component of an artificial joint to bone, said joint having a joint motion surface, said sleeve comprising a body having a longitudinal axis which defines first and second ends, the first end being towards the joint motion surface and the second end being away from the joint motion surface when the sleeve is implanted in the bone, said body having an outer surface which includes a plurality of terraces, each terrace lying in a plane substantially perpendicular to the longitudinal axis, the perimeter of the outer edge of each terrace located in the region of the first end of the body comprising (a) a portion of a circle centered on the longitudinal axis and (b) a portion of an ellipse whose center is offset from the longitudinal axis, said portion of an ellipse, for each of the terraces, (a) being a portion of a common ellipse so that all of the elliptical portions have the same shape, and (b) including a vertex of the ellipse, the perimeters of the terraces located in said first end region having lengths such that for each pair of adjacent terraces, the perimeter of the outer edge of the terrace closer to the first end is longer than the perimeter of the outer edge of the terrace closer to the second end, at least some of said first end perimeters having an oblong form wherein the elliptical portion of the perimeter is half an ellipse and the perimeter includes two lines which are parallel to the ellipse's major axis, and tangent to the ellipse at the ends of its minor axis and spaced from one another by a distance which is less than the diameter of the circular portion of the perimeter.

2. The sleeve of claim 1 wherein successive adjacent terraces have vertices whose locus is a straight line.

3. The sleeve of claim 2 wherein the perimeter of the outer edge of the terraces in the region of the second end of the body consists of a circle centered on the longitudinal axis.

4. The sleeve of claim 2 wherein the outer surface of the body between some pairs of adjacent terraces is undercut so that the perimeter of the inner edge of the terrace closer to the first end is located closer to the longitudinal axis than the perimeter of the outer edge of the terrace closer to the second end.

5. The sleeve of claim 4 wherein the perimeter of the outer edge of the terraces in the region of the second end of the body consists of a circle centered on the longitudinal axis.

6. The sleeve of claim 5 wherein the joint is an artificial hip joint, the sleeve affixes the femoral component of the joint to the femur, and the perimeters of the outer edges of the terraces generally correspond to the inner surface of the femur's hard bone.

7. The sleeve of claim 1 wherein a portion of the outer surface is coated with essentially a single layer of metal balls.

8. A sleeve for affixing a component of an artificial joint to bone, said joint having a joint motion surface, said sleeve comprising a body having a longitudinal axis which defines first and second ends, the first end being towards the joint motion surface and the second end being away from the joint motion surface when the sleeve is implanted in the bone, said body having: (a) an elongated portion centered on and aligned with the longitudinal axis and extending between the first and second ends; and (b) a protruding portion, offset from the longitudinal axis and extending from the first end towards the second end, the cross-sections of the protruding portion in planes substantially orthogonal to the longitudinal axis each including part of an ellipse, each of said parts of an ellipse being a part of a common ellipse so that all of the parts have the same shape, the outer surface of said protruding portion in the region of said elliptically-shaped parts being terraced, at least some of said protruding portion cross-sections having an oblong form wherein the elliptical part is half an ellipse, said half including only one of the ellipse's foci, and the perimeter of said cross-section includes two lines which are parallel to the ellipse's major axis and tangent to the half ellipse at the ends of its minor axis, the minor axis of the ellipse being smaller than the maximum dimension of the elongated portion at the level of the cross-section in a direction parallel to the minor axis of the ellipse.

9. The sleeve of claim 8 wherein the elongated portion is cylindrically-shaped.

10. The sleeve of claim 8 wherein the elongated portion is cone-shaped.

11. The sleeve of claim 10 wherein the outer surface of the cone-shaped portion is terraced.

12. The sleeve of claim 8 wherein the outer surface of the body between terraces is undercut.

13. The sleeve of claim 8 wherein a portion of the outer surface of the body is coated with essentially a single layer of metal balls.

* * * * *